United States Patent
Engel

[19]

[11] Patent Number: 6,099,476
[45] Date of Patent: Aug. 8, 2000

[54] BLOOD PRESSURE MEASUREMENT SYSTEM

[75] Inventor: Stephen J. Engel, East Northport, N.Y.

[73] Assignee: W. A. Baum Co., Inc., Copiague, N.Y.

[21] Appl. No.: 08/950,945

[22] Filed: Oct. 15, 1997

Related U.S. Application Data

[60] Provisional application No. 60/028,627, Oct. 16, 1996.

[51] Int. Cl.[7] ........................................................ A61B 5/02
[52] U.S. Cl. ........................... 600/490; 600/490; 600/494
[58] Field of Search .................................... 600/490, 491, 600/493, 494, 495, 496, 497

[56] References Cited

U.S. PATENT DOCUMENTS

| | | |
|---|---|---|
| 3,308,811 | 3/1967 | Gillette et al. . |
| 3,552,385 | 1/1971 | Janssen . |
| 3,978,848 | 9/1976 | Yen et al. . |
| 4,328,810 | 5/1982 | Hill et al. . |
| 4,356,827 | 11/1982 | Uemura et al. . |
| 4,493,326 | 1/1985 | Hill et al. . |
| 4,658,829 | 4/1987 | Wallace . |
| 4,703,760 | 11/1987 | Miyawaki et al. . |
| 4,727,884 | 3/1988 | Link . |
| 4,747,412 | 5/1988 | Yamaguchi . |
| 4,754,406 | 6/1988 | Miyawaki et al. . |
| 4,793,360 | 12/1988 | Miyawaki et al. . |
| 4,928,701 | 5/1990 | Harada et al. . |
| 4,953,557 | 9/1990 | Frankenreiter et al. . |
| 5,000,187 | 3/1991 | Higuchi et al. . |
| 5,054,495 | 10/1991 | Uemura et al. . |
| 5,201,320 | 4/1993 | Barker . |
| 5,303,711 | 4/1994 | Sciarra . |
| 5,385,149 | 1/1995 | Chang et al. . |
| 5,464,017 | 11/1995 | Juang . |
| 5,467,772 | 11/1995 | Souma . |
| 5,505,206 | 4/1996 | Walloch . |
| 5,533,511 | 7/1996 | Kaspari et al. . |
| 5,535,752 | 7/1996 | Halperin et al. . |
| 5,564,426 | 10/1996 | Iwai . |
| 5,566,676 | 10/1996 | Rosenfeldt et al. . |
| 5,568,814 | 10/1996 | Gallant et al. . |
| 5,649,535 | 7/1997 | Voith . |

*Primary Examiner*—Eric F. Winakur
*Assistant Examiner*—Navin Natnithithadha
*Attorney, Agent, or Firm*—Pennie & Edmonds LLP

[57] ABSTRACT

Blood pressure measurement system for accurately measuring an individual's blood pressure is designed to have a characteristic response corresponding to a typical mercury-gravity pressure manometer. The blood pressure measurement system replaces the mercury column of the standard mercury-gravity pressure manometer with electronic components. The electronic blood pressure measurement system utilizes a pressure transducer connected to a standard pressure cuff and appropriate filtering to augment the output of the pressure transducer such that its characteristic response and damping correspond to the mercury in the mercury-gravity pressure manometer. A display can be utilized to graphically or numerically represent the mercury column as well as providing other useful information. The techniques currently employed for measuring blood pressure with a mercury-gravity pressure manometer may be employed when utilizing the electronic blood pressure measurement system. A method for operating the electronic blood pressure measurement system is also disclosed.

30 Claims, 4 Drawing Sheets

BLOOD PRESSURE MEASUREMENT SYSTEM

This application claims the benefit of U.S. Provisional Patent Application Ser. No. 60/028,627, filed on Oct. 16, 1996.

BACKGROUND OF THE INVENTION

1. Field of the Invention

The present invention relates to blood pressure measurement system, and more particularly to an electronic blood pressure measurement system designed to mimic the characteristic response of mercury-gravity manometers.

2. Discussion of the Background Art

The measurement and monitoring of an individual's blood pressure is an important diagnostic tool in modern medicine. The knowledge of an individual's blood pressure and the periodic monitoring of their blood pressure may be useful in the prevention and treatment of a variety of conditions and/or diseases potentially stemming from high blood pressure (hypertension) or low blood pressure (hypotension). Simply stated, blood pressure is the force that blood exerts on a unit area of the blood vessel walls. During the cardiac cycle, blood pressure varies cyclically with each beat of the heart. The two blood pressure values which are of interest are the systolic and diastolic pressures. The systolic pressure is the pressure that results as a consequence of the "compressive stroke" of the heart, i.e. ventricular systole. Systolic pressure is measured after the ventricles contract to force blood from the heart. The diastolic pressure is the pressure that results as a consequence of the "intake stroke" of the heart, i.e. diastole.

Diastolic pressure is measured after the ventricles relax. Accordingly, the systolic pressure is higher than the diastolic pressure. Typically, both pressure values are represented in millimeters of mercury (mm Hg).

There are a variety of non-invasive blood pressure measurement and monitoring devices currently employed by health care professionals, and a growing number of automatic, non-invasive devices currently available for self-diagnostic purposes. The most widely accepted and utilized device, and the one which is generally utilized as a reference for other devices, is the mercury-gravity pressure manometer commonly referred to as a sphygmomanometer. The sphygmomanometer comprises a pressure cuff and a graded column of mercury. The pressure in the cuff can be varied and is balanced against the column of mercury in order to determine the individual's blood pressure. Essentially, the pressure cuff physically squeezes a part of the body where blood flow may be occluded, and a second device, such as a stethoscope, is utilized to determine when the blood flow has been occluded and when normal blood flow subsequently resumes as a result of varying the pressure in the cuff in accordance with the generally accepted procedure described below.

A technician or other health care professional utilizing the auscultatory method for determining blood pressure places the pressure cuff around an available limb, typically the arm of an adult, and raises the pressure in the cuff until the flow of blood in the limb is occluded and no pulse is felt. The health care professional palpates the artery and increases the pressure in the cuff until the point of obliteration of the pulse is felt by the health care professional. Thereafter, the pressure in the cuff is reduced to zero and then reinflated to approximately 30 mm Hg above the point of obliteration. The pressure in the cuff is then gradually released until the point where a Korotkoff sound is heard by the health care professional with the assistance of a stethoscope. At this point, the pressure in the cuff is equal to the individual's systolic blood pressure. The health care professional makes a mental note of this pressure by reading the graded mercury column. To read this number accurately, the pressure in the cuff must dwell long enough at the correct systolic pressure for the heart to reach a compressive stroke so that a pulse is generated. If the pressure in the cuff is released too rapidly, the systolic pressure reading may be low by as much as the drop in the cuff pressure that occurred between consecutive heart beats. Conversely, if the pressure in the cuff is released too slowly, venous congestion, i.e. arteries constrict faster than veins dilate, may cause an error in the systolic pressure reading. The optimum rate of pressure release in the cuff is 2 to 3 mm Hg per heartbeat. This pressure release rate limits the average systolic pressure error to a range from about 0 to about 1.5 mm Hg. Once the systolic pressure is noted, the health care professional continues to release the pressure in the cuff. As the pressure in the cuff is reduced, the Korotkoff sound changes through several phases. The first phase begins at the systolic pressure and is recognized by a "sharp thud" sound. This sound persists as the pressure in the cuff continuously decreases until the second phase is reached (typically about a 10 mm Hg drop). The second phase is recognized by a "blowing" or "swishing" sound. The second phase Korotkoff sound persists for about a 10 mm Hg drop in cuff pressure. The third phase is characterized by a pulse having a softer thud than the thud heard in the first phase. As the pressure in the cuff continues to decrease, the fourth phase occurs and is characterized by a softer blowing sound that becomes progressively quieter as the pressure in the cuff is reduced until the Korotkoff sound disappears, thereby marking the beginning of the fifth phase. The beginning of the fourth phase marks the first possible diastolic pressure and the beginning of the fifth phase marks the second possible diastolic pressure. Depending upon the health care professionals school of practice, the health care professional simply notes either of these two values by reading the graded mercury column and making a mental note of the value.

Mercury-gravity pressure manometers are extremely accurate devices and offer a number of advantages over other existing blood pressure measuring devices or systems. For example, mercury-gravity pressure manometers provide a clear indication of the cuff pressure release rate. The release rate may be easily determined by watching the mercury slowly descend in the graded column. Another advantage of the mercury-gravity pressure manometer is its response characteristics. Because of the mass of mercury, the hydraulic flow design, and the restrictive air vent at the top of the column, the mercury-gravity manometer responds precisely and smoothly to pressure changes. Accordingly, the mercury in the column will not react, i.e. jump or oscillate, in response to rapid fluctuations in the blood pressure which may be caused by internal or external influences. This characteristic is critical for ensuring proper blood pressure measuring technique thereby providing for extremely accurate and repeatable measurements. The mercury-gravity pressure manometer also has an advantage in that no re-calibration is necessary. While mercury-gravity pressure manometers offer these advantages, their use may be somewhat restricted by size and necessary vertical orientation of the mercury column. For example, if a patient is in a confined area, it may be difficult to utilize a portable mercury-gravity pressure manometer because for normal operation the mercury column has to be positioned vertically and the confined area may only allow the mercury column to be positioned horizontally. In addition, mercury-gravity pressure manometers may not be suitable in gravity-free or reduced gravity environments. For example, mercury-gravity manometers may not be suitable in space applications wherein the gravitational field is not equivalent to the earth's gravitational field.

Other devices may be utilized to measure and monitor blood pressure. Aneroid manometers, for example, may be utilized. In an aneroid manometer, the column of mercury is replaced by a deflectable element such as a Bourdon tube or diaphragm capsule. Unlike mercury-gravity pressure manometers, however, aneroid manometers require frequent calibration because of the wear on the deflectable element and its movement. Additionally, aneroid manometers generally cannot match the desired response characteristics provided by mercury.

Automated blood pressure monitoring has rapidly become an accepted, and in many cases, an essential aspect of human medical treatment. Automated blood pressure monitoring devices are now a conventional part of the patient environment in emergency rooms, intensive and critical care units, and in the operating theater. Less expensive automated blood pressure monitoring devices are also gaining wide acceptance in the home health care market.

An exemplary automated blood pressure monitoring device typically utilizes the point of peak arterial counter pressure oscillations as an indicator of mean arterial pressure. Essentially, the device identifies the peak arterial counter pressure oscillations to determine the mean arterial pressure and then calculates the systolic and diastolic blood pressure values utilizing known algorithms. The monitoring device comprises an automatic inflation pump which inflates a standard pressure cuff to a predetermined pressure limit. If a pulse is detected via a sensor, the pressure cuff is pressurized to a higher value. Once no pulse is detected by the sensor, the pressure in the cuff is decreased incrementally. There is a correlation between the mean arterial pressure and the lowest cuff pressure that yields maximum arterial counter pressure oscillations; accordingly, the mean arterial pressure may be determined by measuring the counter pressure oscillations as the cuff pressure is reduced in discrete increments. A pressure transducer in the pressure cuff may be utilized to detect the arterial counter pressure oscillations. A processor then calculates the systolic and diastolic blood pressures from the mean arterial pressure using the known algorithms.

A typical problem associated with automated blood pressure monitoring devices is that they are not foolproof. The individual undergoing blood pressure measurement and/or continuous monitoring must have a strong enough pulse to be detected by the pressure transducers in the presence of background noise. Background noise can come from the pressure transducers, the electronic support circuitry, vibrations in the room, muscle flexing by the patient, and other sources. Accordingly, the individual should remain motionless during this process because slight movement will cause pressure changes that will be interpreted by the pressure transducers as a pulse. Essentially, the pressure transducers are too responsive in reacting to pressure changes thereby making them oversensitive to transient variations. Therefore, the very individuals that require accurate and continuous blood pressure monitoring are the ones that will get the least accurate readings from automated blood pressure monitoring devices because these individuals often have irregular heart rates and their pulses are not crisp and strong enough for the automated devices to correctly detect and recognize.

A problem associated with automated blood pressure monitoring devices that measure arterial counter pressure oscillations such as described above is the introduction of error causing artifacts due to inadequately or inaccurately sensed counter pressure oscillations. Generally, the arterial counter pressure oscillation signals from the sensor constitute relatively low level, noisy signals superimposed on the much larger, sometimes poorly regulated cuff pressure baseline. Accordingly, these signals are typically passed through band pass filters which are designed to pass the oscillation signals but block noise on the high frequency end and the base cuff pressure and slower variations thereof at the lower end. However, this band pass filtering may contribute further inaccuracy to the counter pressure oscillation detection and measurement process.

Other problems associated with automated blood pressure monitoring devices include a lack of speed and versatility, blood pressure measurement not based on Korotkoff sounds, and prohibitive cost. Automated blood pressure monitoring devices generally cannot be rapidly reset for reuse, nor do they allow the health care professional latitude in use. For example, situations may arise wherein the health care professional wants a quick blood pressure reading based on a transitory condition and the intermittent, fixed interval measurement performed by automated devices simply cannot react quickly enough to catch what may constitute a key blood pressure reading. Automated blood pressure monitoring devices do not utilize Korotkoff sounds for determining blood pressure. Accordingly, the blood pressure readings are typically not as accurate as those that are achieved with standard mercury-gravity pressure manometers. Automated blood pressure monitoring devices are typically expensive devices which unnecessarily raise the cost of health care.

The electronic blood pressure measurement system of the present invention overcomes the limitations associated with the currently utilized measurement devices described above.

SUMMARY OF THE INVENTION

The present invention is directed to a blood pressure measurement system. The blood pressure measurement system comprises a pressure cuff arrangement and an electronics package coupled to the pressure cuff arrangement for measuring the blood pressure of a patient. The pressure cuff arrangement is utilized to manipulate the flow of blood in a limb of the patient. The electronics package can include a pressure transducer, a filter, and a display. The pressure transducer generates an output signal corresponding to the blood pressure of the patient. The filter augments the output signal from the pressure transducer such that its response characteristic corresponds to the response characteristic of mercury in mercury-gravity pressure manometers. The display is utilized to display the blood pressure of the patient.

In accordance with another aspect, the present invention is directed to a electronic blood pressure measurement system comprising a pressure cuff arrangement, at least one pressure transducer, a filter, a display, and a controller. The pressure cuff arrangement is utilized to manipulate the flow of blood in a limb of a patient. The pressure transducer is coupled to the pressure cuff arrangement and generates an output signal corresponding to the blood pressure of the patient. The filter augments the output signal from the pressure transducer such that its response characteristic corresponds to the response characteristic of mercury in mercury-gravity pressure manometers. The display is utilized to display the blood pressure of the patient. The controller implements a number of functions, including controlling the operation of the pressure transducer and the filter, generating images to be displayed on the display, and compensating for errors in the output of the pressure transducer.

The present invention is also directed to an electronics system used by medical personnel for use with a pressure cuff system for a limb of a patient, comprising pressure transducer to generate an output signal corresponding to the blood pressure of the patient; filter adapted to augment the output signal of the pressure transducer such that its response characteristic corresponds to the response characteristic of mercury in mercury-gravity pressure manometers; and display adapted to indicate the blood pressure of the patient.

In accordance with another aspect, the present invention is directed to a method for measuring blood pressure. The method for measuring blood pressure comprises occluding the flow of blood in the limb of a patient until the point of obliteration of the pulse is detected using a pressure cuff arrangement, measuring the pressure in the cuff arrangement as the pressure in the cuff arrangement is reduced to generate an output signal corresponding to the blood pressure of the patient, augmenting the output signal such that its response characteristic corresponds to the response characteristic of mercury in mercury-gravity pressure manometers, compensating for errors in measuring the pressure in the cuff, and displaying the blood pressure of the patient.

Mercury-gravity pressure manometers are utilized as a reference for other blood pressure measuring devices and systems because of their frequency response to pressure changes which results in highly accurate pressure readings. Unlike electronic pressure transducers that typically respond to pressure changes in a millisecond or less, the mercury-gravity pressure manometer is damped in its response because of the mass of the mercury, the hydraulic flow design, and the restrictive air vent at the top of the mercury column. This precise and smooth indication of pressure ensures that the mercury does not jump or oscillate by the pulsing of blood during the various phases of the measuring process, thereby providing highly accurate results, and unlike other techniques, there is no drift, hysteresis, or creep. The electronic blood pressure measurement system of the present invention is designed to mimic the characteristic response and damping of the mercury in mercury-gravity pressure manometer so that blood pressure can be accurately measured utilizing the well known and well established standard measuring technique.

The electronic blood pressure measurement system of the present invention replaces the mercury column of standard mercury-gravity pressure manometers with electronic components, but does not replace the health care professional because the human ear, assisted by a stethoscope, is the best mechanism for detecting the various phases of Korotkoff sounds in the blood pressure measuring process. The mercury column can be replaced with an electronic pressure transducer which senses the pressure in the pressure cuff attached to the limb of the patient, a filter section which receives a signal from the pressure transducer and augments it such that the signal's characteristic response and damping correspond to the mercury in the mercury-gravity pressure manometer, and a display device for displaying the pressure readings. The display may be designed to represent the pressure values graphically and/or numerically. In addition, the pressure release rate may also be displayed, thereby providing a visual cue to the health care professional as to whether the pressure release rate is too fast, too slow, or at the proper release rate. The pressure cuff may also be equipped with a capture button in proximity to the inflation bulb. The capture button may be depressed by the health care professional to electronically capture and display the systolic and diastolic pressures, thereby eliminating the need for the health care professional to make a mental note of the pressure readings. Accordingly, the health care professional may utilize the electronic blood pressure measurement system in a manner analogous to that of a standard mercury-gravity manometer and have the benefit of the additional features without any change in user technique.

The electronic blood pressure measurement system of the present invention also utilizes a controller or microprocessor. In addition to controlling the overall operation of the system, the microprocessor may be utilized to collect and store the systolic and diastolic pressure value readings for each patient. This data may be utilized for historical trending and future reference. The data may then be automatically recalled and displayed for facilitating a rapid diagnosis rather than having the health care professional referring to notes scattered throughout a patient's chart.

The electronic blood pressure measurement system of the present invention provides for an accurate and low cost replacement for or supplement to standard mercury-gravity pressure manometers. The electronic blood pressure measurement system utilizes an electronic pressure sensor augmented by filtering to ensure that the sensor's responsiveness duplicates or corresponds to the response characteristics of mercury-gravity pressure manometers. The electronics utilized in implementing the electronic blood pressure measurement system can be extremely accurate, exhibit substantially no hysteresis, are temperature stable, have negligible internal noise, and provide stable output over extended periods. Additionally, the components utilized are well known and widely used components and are thus relatively inexpensive. Also, since the electronic blood pressure measurement system utilizes electronic components rather than mercury, the system may be utilized in places it could not be previously utilized. For example, since the mercury column has been replaced with electronic components, it can be oriented horizontally, vertically or at any angle therebetween. Therefore, the electronic blood pressure measurement system can be utilized in very confined spaces. In addition, since gravity plays no role in the operation of the electronic blood pressure measurement system, it can be utilized in environments having gravitational fields different from those near or on the earth's surface. For example, the electronic blood pressure measurement system of the present invention may be utilized in space.

The electronic blood pressure measurement system of the present invention is a self-contained, compact, light weight and easily transportable device which may be utilized in any environment where standard mercury-gravity pressure manometers may be utilized and also in places where standard mercury-gravity pressure manometers may not be utilized. The electronic components comprising the electronic blood pressure measurement system may be implemented using solid state technology, thereby ensuring that the measurement system can be implemented in a light weight package. Given its compact and light weight design, the measurement system is highly portable and easy to store. The electronic blood pressure measurement system may be powered from standard external AC power sources with battery backup or it may be operated directly off of battery power, thereby making it more easily transportable, for example, in field use. Alternatively, the electronic blood pressure measurement system may be solar powered. The electronic components are low power components; accordingly, the electronic blood pressure measurement system may be utilized for extended periods on battery power. In addition, since the system utilizes low power components, the system may be safely utilized in operating rooms or other environments which contain potentially combustible materials. The electronic blood pressure measurement system may be packaged in a suitably rigid case that creates a non-obtrusive appearance, is easily cleaned, and which provides protection for the electronic components contained therein. In addition to its nonobtrusive appearance, the electronic blood pressure measurement system of the present invention is manually operated, i.e. a health care professional inflates the pressure cuff arrangement, and thus unlike automated devices, it does not scare patients who may believe that the inflation pump of the automatic devices will not stop, thereby squeezing their arms too tightly.

The electronic blood pressure measurement system of the present invention can be used in the manner in which the standard mercury-gravity pressure manometer is utilized. Since health care professionals can use the same well established measurement technique currently utilized in conjunction with mercury-gravity pressure manometers, little retraining is necessary in order to educate the health care professionals on the additional features available with the electronic blood pressure measurement system. Accordingly, the measurement system can be utilized to measure an individual's blood pressure under any circumstance where a mercury-gravity pressure manometer can be utilized and achieve as accurate results as may be achieved with the standard device. In the hands of a less experienced health care professional, potentially more accurate results may be achieved because the health care professional does not have to interpret the meniscus of the mercury while it is in motion. Rather, the health care professional just has to glance at the graphical or numerical display to read the pressure values. In addition, with the capture button available to display and save the results of the measured systolic and diastolic pressures, the health care professional is not distracted and can monitor the cuff pressure release rate to ensure that it is at the proper rate while listening for pulse or Korotkoff sound changes.

BRIEF DESCRIPTION OF THE DRAWINGS

The present invention is described in detail below with reference to the drawings in which.

DETAILED DESCRIPTION OF THE PREFERRED EMBODIMENTS

In the description which follows, any reference to either direction or orientation is intended primarily and solely for the purposes of illustration and is not intended in any way as a limitation to the scope of the present invention. Also, the particular embodiments described herein, although being preferred, are not to be considered as limiting of the present invention.

The present invention is directed to an electronic blood pressure measurement system designed to mimic the characteristic response and damping of the mercury in standard mercury-gravity pressure manometers. The electronic blood pressure measurement system comprises a pressure cuff arrangement, including an inflatable bladder and an inflation bulb for varying the pressure in the inflatable bladder, and an electronics package, including a pressure transducer, a filter section, a display and a controller. The pressure transducer is coupled to the pressure cuff arrangement and outputs a signal indicative of the pressure in the cuff. This signal is augmented by the filter section such that its characteristic response and damping are equivalent to that of the mercury in the mercury-gravity pressure manometer. The augmented signals may be stored for future reference and/or for display in real time on the display. The controller controls the overall operation of the system. The electronic blood pressure measurement system may be utilized in a manner analogous to the use and with the same procedures associated with standard mercury-gravity pressure manometers.

Figure 1:
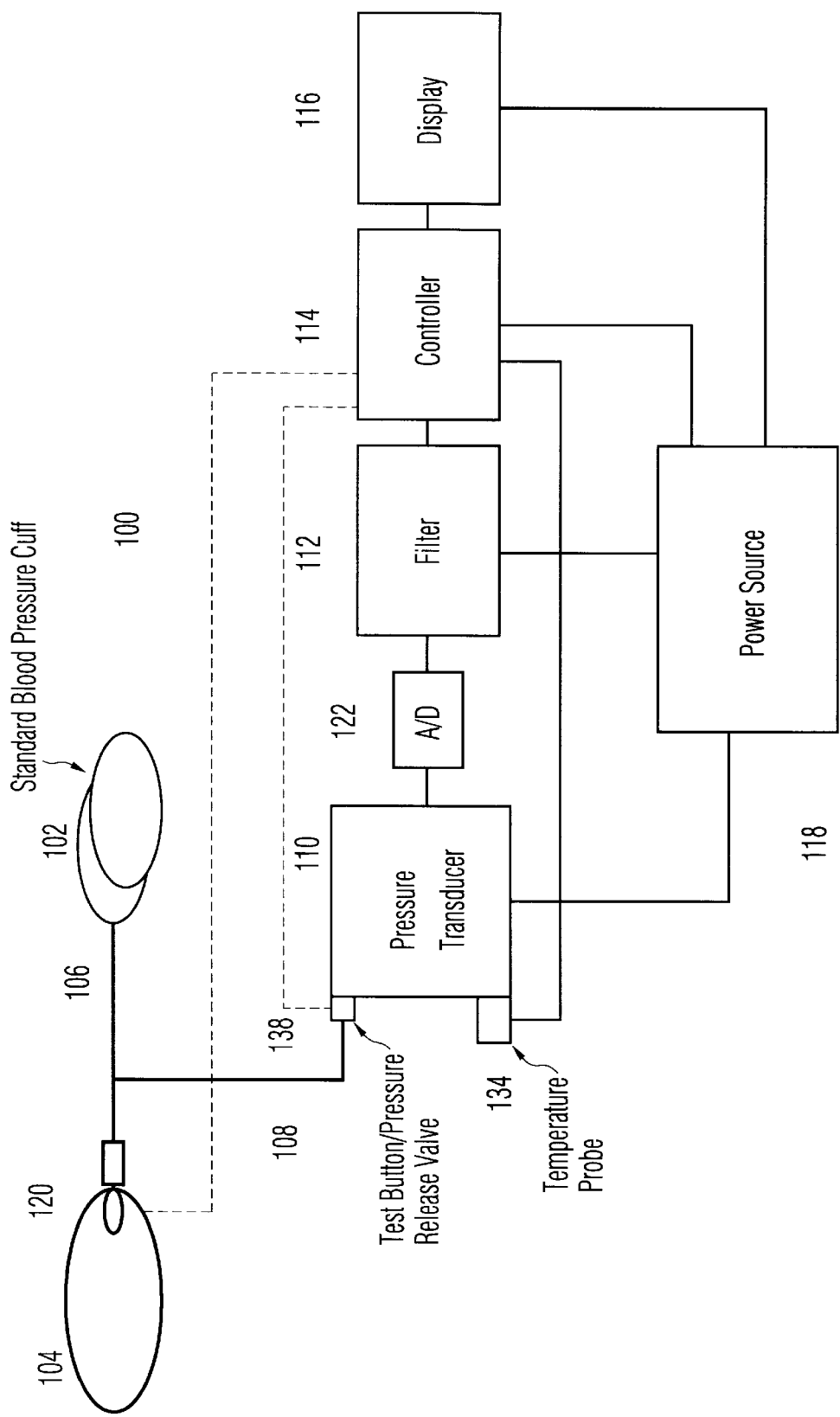
FIG. 1 is a block diagram representation of an exemplary embodiment of the electronic blood pressure measurement system of the present invention.

FIG. 1 is a block diagram representation of an exemplary embodiment of a blood pressure measurement system 100 in accordance with the present invention. As illustrated, the pressure cuff arrangement or system comprise an inflatable bladder 102 and an inflation bulb 104 connected through a first pressure hose 106. The pressure cuff arrangement may be coupled to the electronics package through a second pressure hose 108. The electronics package comprises a pressure transducer 110, a filter section 112, a controller 114, and a display 116. The electronics package may also comprise a power source 118. The second pressure hose 108 may be connected between the first pressure hose 106 and an input pressure port of the pressure transducer 110 by any suitable means which will ensure a pressure tight seal.

The inflation bulb 104 and the inflatable bladder 102 comprising the pressure cuff arrangement may be identical to the components utilized in conjunction with standard mercury-gravity pressure manometers. However, rather than the pressure cuff arrangement being connected to a graded column of mercury to represent the pressure in the inflatable bladder 102, the pressure cuff arrangement is connected to the pressure transducer 110 which represents the pressure in the inflatable bladder 102 as an electrical signal, e.g. a current or a voltage signal, which may be utilized to generate a graphical or numerical display. The inflation bulb 104 may be modified to include a capture button 120, the function of which is discussed in detail subsequently. The capture button 120 may be attached to the inflation bulb 104 at any suitable location wherein a system operator, e.g. a health care professional, may easily depress the capture button 120 to capture and save the systolic and diastolic blood pressure value readings. The capture button 120 may also be connected to the controller 114 via an electrical lead. In alternative embodiments, the capture button 120 may be implemented as a foot actuated switch or a voice actuated switch rather than as a hand or finger actuated switch attached to the inflation bulb 104.

The pressure transducer 110 comprises an electronic pressure transducer operable to convert pneumatic pressures from the inflatable bladder 102 into corresponding electrical signals. The pressure transducer 110 may be connected to the pressure cuff arrangement at any suitable location for determining the pressure in the inflatable bladder 102. In the illustrated embodiment, the pressure transducer 110 is connected to the first pressure hose 106 via the second pressure hose 108. The pressure transducer 110 preferably measures and converts pressure values ranging from 0 mm Hg to 300 mm Hg, generally referred to as the operating range, into electrical signals with minimal error. Electronic pressure transducers are typically very accurate exhibiting excellent linearity (deviation is less than 0.2 percent of full scale), practically no hysteresis (less than 0.05 percent of full scale), negligible internal noise (0.04 mm Hg peak to peak, 0.01 to 10 Hz), and long term stability (0.1 percent of full scale over a one year period). Accordingly, the total error which may be introduced by the pressure transducer 110 is a deviation of about 1 to 1.5 percent of full scale. A deviation of 1 to 1.5 percent of full scale corresponds to about 3 to 4.5 mm Hg, which may be significant for some accurate blood pressure measurement. Accordingly, in order to achieve more accurate results, this minimal error may be compensated for by configuring the controller 114 to reduce or substantially eliminate the error as is explained in detail subsequently. The pressure transducer 110 may output either a current signal or a voltage signal indicative of the pressure in the inflatable bladder 102. The electrical signal output from the pressure transducer 110 is input to the filter section 112 via an electrical signal line. Although FIG. 1 illustrates an analog to digital converter 122 positioned between the pressure transducer 110 and the filter section 112, no analog to digital converter is necessary if the filter section 112 comprises an analog filter as is explained in detail subsequently.

In an alternative embodiment, more than one pressure transducer may be utilized. Multiple pressure transducers may be utilized to obtain a single electrical output signal indicative of the pressure in the inflatable bladder 102. For example, if two pressure transducers are utilized, the average of the two output signals may be input to the filter section 112. Alternatively, if three pressure transducers are utilized, a voting or averaging method may be established to generate a single output signal indicative of the pressure in the inflatable bladder 102 for input to the filter section 112. For example, if a voting method is utilized, the output signals of two of the three pressure transducers may be compared and if the signals do not correspond within a predetermined tolerance, the output value from the third pressure transducer may be compared to each of the other two output signals to determine if there is a correspondence. Additional analog circuitry may be used to implement the averaging or voting method if more than a single pressure transducer is utilized. Preferably, a microprocessor or micro controller, rather than analog circuitry, would be programmed to implement the voting or averaging method and thereby reduce the amount of hardware utilized.

The filter section 112 may, as explained above, be utilized to augment the electrical signal output from the pressure transducer 110 such that the signal's characteristics mimic the characteristic response and damping of the mercury in mercury-gravity pressure manometers. The filter section 112 may be implemented in any number of ways. For example, the filter section 112 may be implemented as an analog device utilizing active and passive components such as differential amplifiers, resistors, capacitors and inductors. Alternatively, the filter section 112 may be implemented as a digital device utilizing digital signal processing algorithms implemented by a microprocessor. In a preferred embodiment, the filter section 112 is a digital filter implemented by a microprocessor using standard digital signal processing techniques. The digital filter may be implemented on a dedicated microprocessor or it may be implemented by the controller 114 as explained in detail subsequently.

A typical electronic pressure transducer has a response time of a millisecond or less. Therefore, these devices are too responsive and would make blood pressure readings subject to pressure noise. For example, electronic pressure transducers can react to pressure changes in excess of 200 mm Hg in 1 millisecond making them oversensitive to transient variations. Since the mercury in a mercury-gravity pressure manometer responds slowly, i.e. low frequency response, because of the mass of mercury, the hydraulic design of the mercury column, and the restrictive air vent at the top of the column of mercury, the mercury-gravity pressure manometer is not subject to transient pressure variations and is thus very accurate. Accordingly, the output of the pressure transducer 110 is preferably augmented to achieve the equivalent response and damping characteristics of the mercury in the mercury-gravity pressure manometer. In order to augment the output signal from the pressure transducer 110 such that its output characteristic mimics or corresponds to that of mercury in a mercury-gravity pressure manometer, the electrical signal from the pressure transducer 110 is preferably augmented by a low pass filter. A low pass filter is utilized so that only the low frequency portion of the output signal from the pressure transducer 110 is passed therethrough for use as the blood pressure reading, while the higher frequency portions of the output signal, which would introduce jitter or bounce in the blood pressure readings, are attenuated. The cutoff frequency of the low pass filter can be selectively predetermined to correspond to a standard mercury-gravity pressure manometer as a reference.

A low pass digital filter may be implemented utilizing a number of digital signal processing techniques ranging from highly sophisticated processes in which the complex frequency and phase of the signal to be filtered are of concern, to less sophisticated techniques which are concerned only with the non-complex frequency of the signal to be filtered. In the measurement of blood pressure, only the low, non-complex frequency portion of the signal is of importance for the reasons discussed above. Accordingly, the low pass filter may be implemented utilizing a standard digital signal processing technique. One exemplary digital signal processing technique for low pass filtering is to output a value that equals the moving average of n input values as sampled over a fixed interval of time. For example, if n equals 5, the five most recent samples are added together and the sum is divided by five. The cutoff frequency of the low pass digital filter can be changed by changing the window n. For example, to lower the cutoff frequency, the window or value of n can be increased, whereas to raise the cutoff frequency, the window or value of n can be decreased. The result of this filtering operation is an electrical signal which accurately represents the systolic or diastolic blood pressure of a patient. This electrical signal can then be stored and/or displayed by the controller 114. Essentially, the low pass digital filter of the filter section 112 changes the display's 116 response to changes in the pressure transducer's 110 output caused by pressure transients. Accordingly, as in standard mercury-gravity pressure manometers where the mercury does not bounce or oscillate, the displayed blood pressure readings from the electronic blood pressure measurement system also do not bounce or oscillate.

Since the filter section 112 preferably comprises a digital low pass filter, an analog to digital converter 122 may be utilized to convert the output signals from the pressure transducer 110, which are analog signals, into digital signals suitable for processing by the microprocessor implementing the digital filtering algorithm. The analog to digital converter 122 may be a stand alone device or it may be integrated within the microprocessor which implements the filtering algorithm. If the frequency content of the signal output from the pressure transducer 110 exceeds twice the sampling rate of the particular analog to digital converter 122, an anti-aliasing filter is preferably utilized. An anti-aliasing filter is a low pass filter with a cut-off frequency set to eliminate sensor signal frequencies above the sampling frequency of the analog to digital converter 122. The anti-aliasing filter can be implemented using standard analog components and positioned between the pressure transducer 110 and the analog to digital converter 122 of the filter section 112. If the frequency content of the signal output from the pressure transducer 110 does not exceed the above limit, no anti-aliasing filter is required.

Alternative embodiments may be utilized to convert the output signal of the pressure transducer 110 into a usable digital signal for filtering by the digital low pass filter. For example, a suitable circuit to utilize for this purpose is a voltage controlled oscillator and a frequency counter. The voltage or current signal output signal from the pressure transducer 110 is converted into a frequency signal by the voltage controlled oscillator. The frequency counter counts the number of pulses during a controlled interval of time. This number is then low pass filtered as described above.

The output of the filter section 112, i.e. the augmented signal from the pressure transducer 110, may be input into the controller 114. The controller 114 controls the overall operation of the other components comprising the electronic blood pressure measurement system 100, including compensating for the inaccuracies in the pressure transducer 110, capturing the blood pressure values, maintaining and storing the collected blood pressure values, and controlling the display 116. The controller 114 may comprise any suitable device for performing these operations. In the preferred embodiment, the controller 114 comprises a microprocessor including the appropriate input/output devices and configuration and associated memory. As previously suggested, in the preferred embodiment, the filter section 112 comprises a low pass digital filter which is implemented on a microprocessor; accordingly, two separate and distinct microprocessors may be utilized to implement the filtering and the control and display functions, or a single microprocessor may be programmed or configured to implement both the filtering and the control and display functions. Although the filter section 112 and the controller 114 are illustrated in FIG. 1 as separate components of the electronic blood pressure measurement system 100, this is for ease of explanation, and in a preferred embodiment, the microprocessor of the controller 114 implements the low pass digital filter as well as all the control and display functions described herein.

Figure 2:
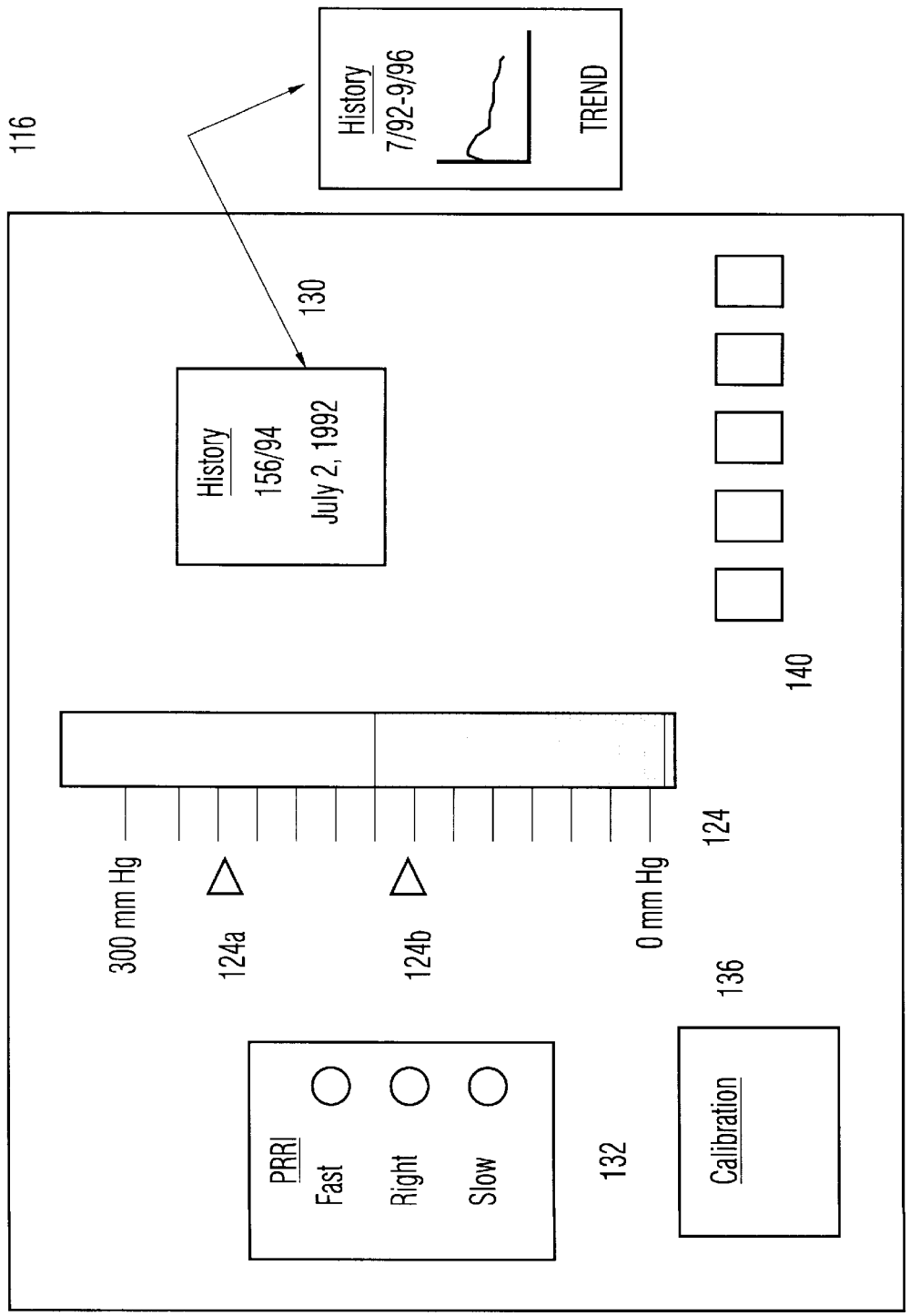
FIG. 2 is a diagrammatic representation of a first exemplary embodiment of a display of the electronic blood pressure measurement system of the present invention.
Figure 3:
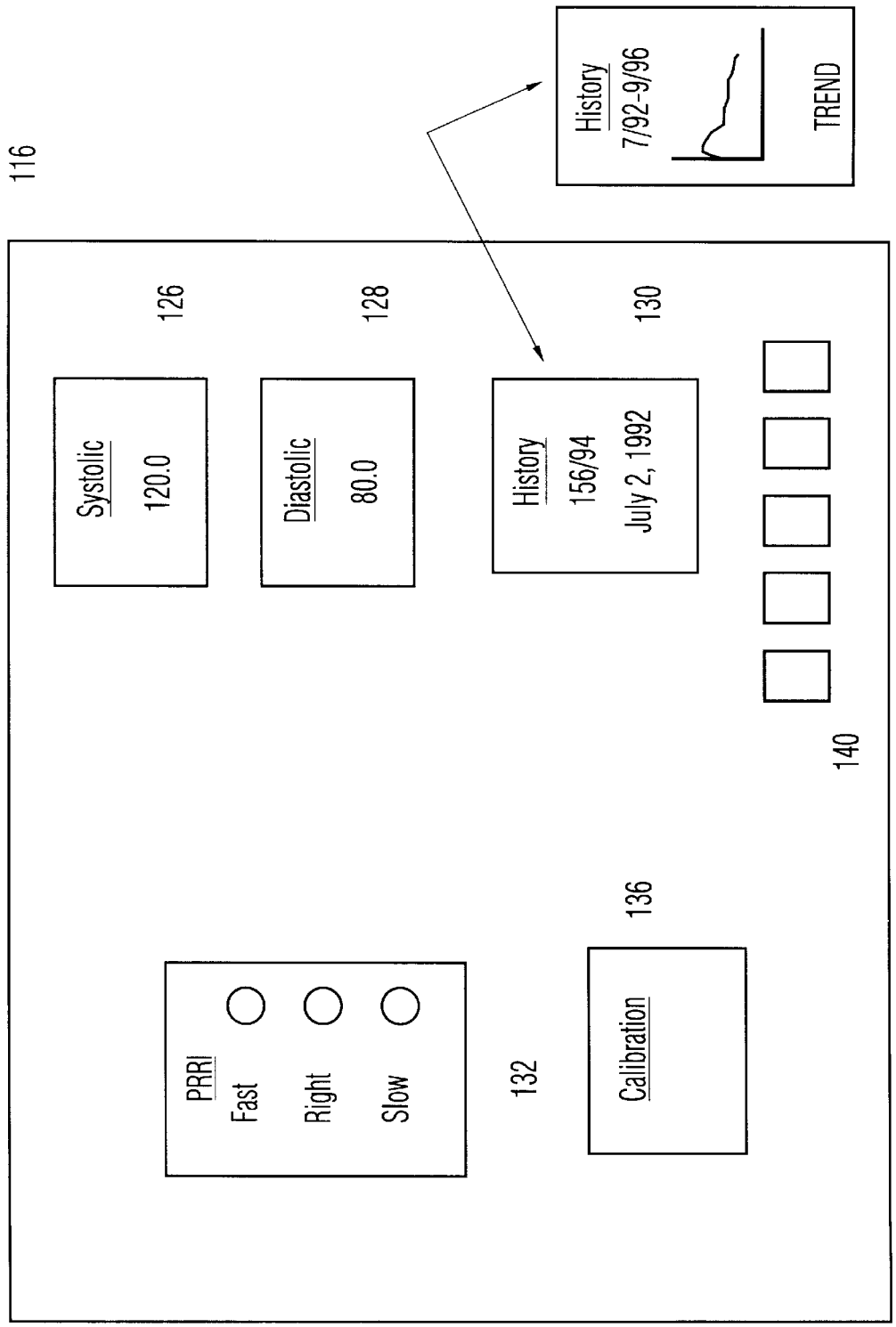
FIG. 3 is a diagrammatic representation of a second exemplary embodiment of a display of the electronic blood pressure measurement system of the present invention.
Figure 4:
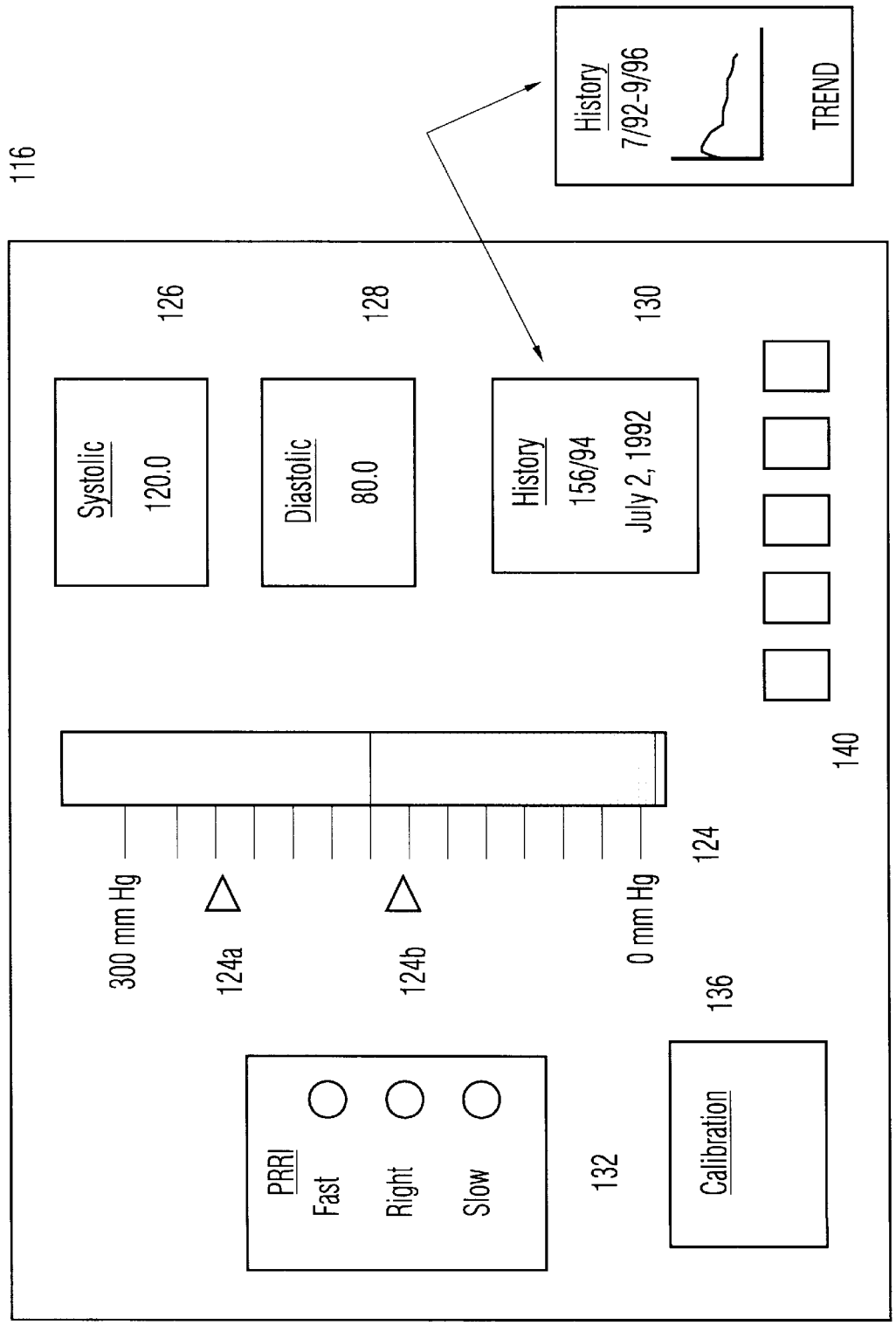
FIG. 4 is a diagrammatic representation of a third exemplary embodiment of a display of the electronic blood pressure measurement system of the present invention.

The controller 114 may be programmed or configured to output the blood pressure readings obtained from the low pass filtering of the signals output by the pressure transducer 110 in a number of ways. For example, the controller 114 may be configured to generate a graphical image or representation of a graded mercury column for display on the display 116 which moves in response to pressure changes in the inflatable bladder 102 in a manner analogous to the movement of the mercury in a standard mercury-gravity pressure manometer. As described above, the graphical representation of the graded mercury column will respond to pressure changes in the inflatable bladder 102 with response and damping characteristics corresponding to that of the mercury in the mercury-gravity pressure manometer. Accordingly, the health care professional can simply monitor the displayed graphical representation in the same manner as he or she would monitor the actual mercury in a graded column to determine the systolic and diastolic blood pressures. FIG. 2 illustrates the display 116 with a graphical representation of a graded mercury column 124 displayed thereon. Alternatively, the controller 114 can be configured or programmed to generate a display of two sets of numerical values, i.e. one for the systolic blood pressure and one for the diastolic blood pressure, for display on the display 116, and whose values change in response to changes in the pressure in the inflatable bladder 102. The changes in the numerical values would change in a manner comparable to the movement of the mercury in a mercury-gravity pressure manometer because of the filtering. In other words, rather than the controller 114 generating a graphical representation of a graded mercury column from which the pressure readings can be monitored by the health care professional, a numerical display of the two sets of pressure readings may be generated. Essentially, the health care professional can monitor the numerical display, rather than monitoring a moving graphical representation of a mercury column, to determine the systolic and diastolic blood pressure readings. FIG. 3 illustrates the display 116 having two numeric display regions 126 and 128 with two sets of numerical blood pressure values displayed thereon. In yet another alternative embodiment, both a graphical representation of a graded mercury column 124 and two sets of numerical displays 126 and 128 can be utilized as illustrated in FIG. 4. The controller 114 can be configured with known programs for generating both graphical and numerical representations for display on the display 116.

As an alternative to having the health care professional continuously monitoring the graphic representation or numerical representation displayed on the display 116, the health care professional can simply depress the capture button 120 on the inflation bulb 104 at the appropriate times to capture the systolic and diastolic blood pressure readings. Essentially, whereas the health care professional would have to make a mental note of the blood pressure readings after glancing at the mercury column in a standard mercury-gravity pressure manometer, he or she can now simply press a button and the values can be recorded by the microprocessor of the controller 114 and saved in the memory associated therewith. In addition, as noted above, the capture button 120 can comprise other suitable devices such as foot actuated devices or voice actuated devices. These alternate switching devices can be implemented in a known manner. The capture button 120, in whatever form, functions to save the pressure reading at that instant in time. When the capture button 120 is depressed, the pressure in the inflatable bladder 102 at that instant in time can be stored in a nonvolatile memory associated with the microprocessor of the controller 114. In addition to storing the pressure reading, the controller 114 can be configured to display, graphically or numerically, the captured pressure reading on the display 116. For example, if a graphical representation of a graded mercury column 124 is utilized as illustrated in FIGS. 2 and 4, some type of markers may be positioned in proximity to the graphical representation, i.e., along the graded mercury column image 124, to demark the systolic and diastolic blood pressure values. For example, pointers 124a and 124b can be utilized to demark the systolic and diastolic blood pressure readings. Alternatively, if numerical displays are utilized, the value in numerical display 126 is frozen when the capture button 120 is first depressed and the value in numerical display 128 is frozen when the capture button 120 is depressed a second time. The stored pressure values can be utilized for historical trending, or simply recalled at a later time or date for comparison with the present blood pressure readings. Accordingly, a separate area of the display 116, designated as the historical data display area 130, can be utilized to display the trend of previous blood pressure readings over a given period of time or simply the previous pressure readings for this patient and the date the readings were taken as illustrated in FIGS. 2–4. The capture button 120 can comprise any standard electrical switch or button which can be easily manipulated using only one hand. The controller 114 can be easily programmed to save, store, and display "snapshot" pressure readings as well as to generate trends from the current and historical data collected.

The controller 114 can also be programmed or configured to monitor the pressure release rate of the pressure in the inflatable bladder 102. As discussed above, to ensure accurate blood pressure measurements, the pressure in the inflatable bladder 102 is preferably released at a rate of 2 to 3 mm Hg per heartbeat. This pressure release rate is currently determined by the health care professional monitoring the mercury as it moves within the graded column of the standard mercury-gravity pressure manometer, and can still be done in this manner by monitoring the movement of the graphical representation of the mercury column 124 on the display 116 or the changes in the numerical displays 126, 128. However, the controller 114 can be configured to output a signal, either audio, visual, or both audio and visual, which indicates that the pressure release rate is too fast, too slow, or at the preferable rate of 2 to 3 mm Hg per heartbeat. For example, a portion of the display 116 may be designated as a pressure release rate indicator (PRRI) 132 as illustrated in FIGS. 2–4. The pressure release rate indicator 132 can comprise a three position gauge corresponding to the three release rate possibilities as illustrated in FIGS. 2–4. Preferably, the gauge of the pressure release rate indicator 132 may comprise more than three positions so that the degree of imprecision in pressure release rate can be determined. For example, additional positions on the gauge may indicate slightly faster, much faster, slightly slower, or much slower rates. In yet another alternative embodiment, the pressure release rate indicator 132 can be configured as a full linear gauge which indicates the actual pressure release rate as calculated by the controller 114. The health care professional can then simply glance up at the display 116 every so often to determine if the pressure in the inflatable bladder 102 is being released at the proper 2 to 3 mm Hg per heartbeat rate. A suitable program which calculates the rate of pressure change and compares the result of this calculation with the predetermined pressure release rate can be readily implemented on the microprocessor of the controller 114.

The controller 114, as described above, can also be programmed or configured to compensate for pressure transducer inaccuracies. The majority of factors which contribute to the inaccuracy of the pressure transducer 110, including linearity error, hysteresis error, drift error, and error introduced due to variations in the supply current or voltage are known quantities or quantities that can be readily determined. Accordingly, these errors can be easily compensated for by the controller 114 as explained in detail subsequently. The effects of temperature variations, e.g. the effect of temperature changes on offset and the effect of temperature changes on the span of the pressure transducer 110, can be measured and as such are known quantities at any given instant in time and thus can be compensated for by the controller 114 in a similar manner. Basically, the known quantities and the measured quantities can be utilized by the controller 114 to correct the errors in the signals from the pressure transducer 110 by a simple correction process or algorithm.

There are a number of processes which can be implemented by the controller 114 to compensate for the inaccuracies in the signals output from the pressure transducer 110. One simple exemplary error correction process comprises an interpolation algorithm. The interpolation algorithm can comprise a linear interpolation function or a non-linear or higher order interpolation function depending on the quality of the pressure transducer utilized. High quality pressure transducers generally have a linear output response over a given operating temperature range, whereas lesser quality pressure transducers typically have non-linear output responses over a given operating temperature range. Preferably, the pressure transducer 110 has a linear output response over a broad operating temperature range. Through a calibration process, a function describing the output of pressure transducer 110 for different input pressures and at least two operating temperatures can be developed. This function, as stated above, can be linear or non-linear. Since it may be impractical to perform this calibration process at every incremental point over the entire possible operating temperature range, a linear or non-linear interpolation process may be utilized to determine the actual pressure from the output of the pressure transducer 110. In order to illustrate the error correction process, it can be assumed that the output of the pressure transducer 110 is linear over the operating temperature range; therefore, the pressure transducer 110 output may be given by: sensor value= slope*actual pressure+offset, which is the equation for a line. The sensor value is the output of the pressure transducer 110 and the slope and offset are variables which can change as the temperature of the pressure transducer 110 changes. Utilizing a test or calibrated pressure source, slope and offset values are calculated for a predetermined number of temperature values. These values can be stored in the memory of the microprocessor of the controller 114, preferably as a table. Accordingly, during normal operation of the electronic blood pressure measurement system 100, the actual blood pressure may be determined from the output of pressure transducer 10 using the above equation. The values for slope and offset for a given operating temperature are stored in memory and the sensor value is also a known quantity and thus the actual pressure may be determined by the microprocessor of the controller 114 implementing the above equation. As stated above, it is impractical to store a slope and offset for each incremental step in operating temperatures; accordingly, if the particular operating temperature does not correspond to a value stored in memory, a linear interpolation can be utilized by the microprocessor of the controller 114 to obtain slope and offset values. If it has been determined that the output of the pressure transducer 110 is not linear, then a function describing the relationship between the actual pressure and the pressure from the pressure transducer 110 can be developed and a corresponding non-linear interpolation used to fill in the missing data in a manner to that described above.

The output signal from the pressure transducer 110 can first be filtered and then undergo error correction as described above, or the output signal can first undergo error correction and then be filtered with substantially the same results. In the preferred embodiment, the output signal is first filtered and then subjected to the error compensation process described above.

In order to accurately measure the temperature of the pressure transducer 110 during operation, at least one temperature probe 134 is preferably positioned in proximity to the pressure transducer 110. Any suitable device can be utilized for measuring the temperature of the pressure transducer 110. For example, the temperature probe 134 may comprise a resistive device, a thermocouple, a thermistor, or a semiconductor temperature probe. In a preferred embodiment, a single semiconductor probe 134 may be positioned on the pressure transducer 110 to measure the temperature thereof. Semiconductor temperature probes are three terminal devices capable of outputting 10 millivolts per degree Fahrenheit; accordingly, a high degree of resolution may be obtained from the device. The semiconductor temperature probe 134 can be mounted to the pressure transducer 110 by any suitable means which has a sufficiently high coefficient of thermal conductivity, such as a thermal grease or adhesive. The electrical signals output from the semiconductor temperature probe 134 may be fed back to the controller 114 for use as described above.

The controller 114 can also be programmed or configured to provide a self calibration function. For example, the microprocessor of the controller 114 can be programmed to compare an output signal from the pressure transducer 110 after being corrected by the compensation process described above with a preselected value. Preferably, the pressure at the pressure input port of the pressure transducer 110 may be reduced to a value of 0 mm Hg thereby ensuring an easily obtainable, known pressure value. Then the compensated output signal from the pressure transducer 110 can be compared with the preselected value, which in this case is 0 mm Hg and the current temperature of the pressure transducer 110 as measured by the temperature probe 134. If the values are substantially equal or differ by less than a predetermined amount, the electronic blood pressure measurement system 100 can be immediately utilized. Essentially, for 0 pressure at the input port of the pressure transducer 110, one would expect an output signal from the pressure transducer 110 to correspond to 0 mm Hg after compensation. If however, the values are different by more than the predetermined amount, the electronic blood pressure measurement system 100 may require calibration prior to use. Re-calibration may simply require updating the data in the memory of the microprocessor of the controller 114 to reflect the changes in the pressure transducer 110 output caused by use over many cycles of operation. A portion of the display 116 may be utilized to display a calibration indication flag 136, as illustrated in FIGS. 2–4, when calibration is needed. In addition, the controller 114 may be programmed or configured to keep track or maintain a record of the number of blood pressure measurement cycles for which the system has been utilized. Once a certain count has been achieved or exceeded, a flag may displayed on the display 116 indicating that it would be preferable that the system be calibrated.

The pressure at the pressure input port of the pressure transducer 110 may be reduced to 0 mm Hg and the self calibration function initiated by a test button/pressure release valve 138. The test button/pressure release valve 138 may comprise an automatically actuated valve or a manually actuated valve. For example, the test button/pressure release valve 138 may comprise an automatically actuated solenoid valve. Accordingly, the solenoid valve may be open and closed via commands from the controller 114. In a preferred embodiment, the test button/pressure release valve 138 comprises a manually actuable valve. For example, the test button/pressure release valve 138 may comprise a check valve similar to the type of valve utilized in tires. Accordingly, the pressure at the pressure input port of the pressure transducer 110 may be reduced to 0 mm Hg by simply depressing the stem of the test button/pressure release valve 138. In addition, pressing the test button/pressure release valve 138 also transmits a signal to the controller 114 to initiate the above described self calibration function.

The display 116 may comprise any suitable device for providing graphical, numerical, or a graphical and numerical displays. For example, the display 116 may comprise a cathode ray tube, a liquid crystal display, an array of miniature incandescent light bulbs, or a light emitting diode display. Regardless of the particular medium utilized to implement the display 116, if a graphic display of a graded mercury column is desired, the display 116 should preferably be large enough to accommodate a graphical representation of a graded mercury column having an operating range of 0 mm Hg to 300 mm Hg in 2 mm Hg increments such that its accuracy equals that of the graded mercury column in a standard mercury-gravity pressure manometer. For enhancing the precision of the graphical representation of the graded mercury column, the displayed operating range of 0 mm Hg to 300 mm Hg may be divided into 1 mm increments. If only a numeric display is utilized, then the size of the display 116 may be greatly reduced. In addition, with the numeric display, the precision can be taken out to as many decimal places as desired. In a preferred embodiment, the display 116 comprises a liquid crystal display which may be utilized to provide both a graphical representation of a graded mercury column and a numeric display for both the systolic and diastolic blood pressure readings as well as all of the other displays described above. A liquid crystal display may be preferable because of its low power consumption and its ability to provide high resolution image displays. In an alternative embodiment, the display 116 may comprise one or more meter type indicators. For example, electrical meter needle movement may be utilized to indicate the systolic and diastolic blood pressure values. A deflection type meter such as a galvanometer, a voltmeter, and/or an ammeter may be utilized for any of the above described displays. The microprocessor of the controller 114 may be programmed in a known manner to generate any of the above described displays.

The power supply circuitry 118 may comprise any suitable means for supplying reliable power for the other components comprising the electronics package. The electric blood pressure measurement system may be operated from battery power or from standard AC power. In addition, a battery back-up may be provided. Accordingly, the power supply circuitry 118 comprises circuitry for converting the power from a standard AC receptacle to voltage, current and frequency levels suitable for the remaining components of the electronics package as well as circuitry for providing a seamless bridge to battery backup power when there is a fault detected in the AC power. The battery utilized may comprise any suitable rechargeable battery. In addition to, or in the alternative, the power supply circuitry 118 may comprise a solar energy conversion circuit. For example, solar cells similar to the cells utilized in calculators and other smaller scale electronic devices may be utilized to provide power for the components comprising the electronics package of the electronic blood pressure measurement system.

The electronics package comprises the pressure transducer 110, the filter section 112, the controller 114, the display 116 and the power supply circuitry 118. The temperature probe 134 and the pressure release valve 138 may be coupled to the pressure transducer 110. The capture button 120, which may be attached to the inflation bulb 104 of the pressure cuff arrangement, is electrically connected to the electronics package, but is not part of the electronics package itself. All components comprising the electronics package can be housed within a single, light weight and compact package which is suitable for use in any environment, including emergency room and operating theaters. The display 116 may function as a cover for the package in much the same manner as the display in a lap top computer. Control commands and display commands can be input through switches positioned on any suitable area of the package. For example, hard switches 140 may be positioned in an area below the display 116 as illustrated in FIGS. 2–4. Alternatively, the switches may be software switches as part of the display itself, e.g. touch bezel switches. In yet another alternative embodiment, a keyboard may be utilized. The keyboard may be built into the controller 114 in much the same manner as the keyboard in a lap top computer.

Although shown and described is what is believed to be the most practical and preferred embodiments, it is apparent that departures from specific designs and methods described and shown will suggest themselves to those skilled in the art and may be used without departing from the spirit and scope of the invention. The present invention is not restricted to the particular constructions described and illustrated, but should be construed to cohere with all modifications that may fall within the scope of the appended claims.

What is claimed is:

1. Blood pressure measurement system for use by medical personnel comprising:

pressure cuff system for a limb of a patient; and electronics package coupled to said pressure cuff system, the electronics package including a pressure transducer adapted to generate an output signal corresponding to the blood pressure of the patient, a filter adapted to augment the output signal of the pressure transducer such that its response characteristic corresponds to the response characteristic of mercury in mercury-gravity pressure manometers, a controller adapted to compensate for errors in the output of said pressure transducer, and a display adapted to indicate the blood pressure of the patient.

2. The blood pressure measurement system according to claim 1, wherein said pressure cuff system comprises an inflation bulb and an inflatable bladder.

3. The blood pressure measurement system according to claim 1, wherein said filter comprises a digitally implemented low pass filter.

4. The blood pressure measurement system according to claim 1, wherein said display comprises a liquid crystal display.

5. The blood pressure measurement system according to claim 1, wherein said display comprises a light emitting diode array.

6. The blood pressure measurement system according to claim 1, wherein said controller is adapted to control the operation of said pressure transducer and said filter, and to generate images on said display.

7. The blood pressure measurement system according to claim 6, wherein said controller comprises a microprocessor and associated memory.

8. The blood pressure measurement system according to claim 7, wherein said controller comprises an analog to digital converter.

9. The blood pressure measurement system according to claim 7, further comprising a capture button coupled to said controller, said capture button being operable to store the blood pressure of the patient in the memory of said controller and to display the blood pressure on said display when actuated.

10. The blood pressure measurement system according to claim 1, further comprising a power supply.

11. An electronic blood pressure measurement system for use by medical personnel comprising:

pressure cuff arrangement for manipulating blood flow in a limb of a patient;

at least one pressure transducer coupled to the pressure cuff arrangement and adapted to generate an output signal corresponding to the blood pressure of the patient;

filter for augmenting the output signal of said at least one pressure transducer such that its response characteristic corresponds to the response characteristic of mercury in mercury-gravity pressure manometers;

display adapted to display the blood pressure of the patient; and controller adapted to implement a plurality of functions including controlling the operation of said at least one pressure transducer and said filter, generating images on said display, and compensating for errors in the output of said at least one pressure transducer.

12. The electronic blood pressure measurement system according to claim 11, wherein the pressure cuff arrangement comprises an inflation bulb and an inflatable bladder.

13. The electronic blood pressure measurement system according to claim 11, wherein said filter comprises a digitally implemented low pass filter.

14. The electronic blood pressure measurement system according to claim 11, wherein said display comprises a liquid crystal display.

15. The electronic blood pressure measurement system according to claim 11, wherein said display comprises a light emitting diode array.

16. The electronic blood pressure measurement system according to claim 11, wherein said controller comprises a microprocessor and associated memory.

17. The electronic blood pressure measurement system according to claim 16, wherein said controller comprises an analog to digital converter.

18. The electronic blood pressure measurement system according to claim 16, further comprising a capture button coupled to said controller, said capture button being operable to store the blood pressure of the patient in the memory of said controller and to display the blood pressure on said display when actuated.

19. The electronic blood pressure measurement system according to claim 11, further comprising a power supply.

20. An electronics system for use by medical personnel with a pressure cuff system for a limb of a patient, comprising:

a. pressure transducer to generate an output signal corresponding to the blood pressure of the patient;

b. filter adapted to augment the output signal of said pressure transducer such that its response characteristic corresponds to the response characteristic of mercury in mercury-gravity pressure manometers;

c. controller adapted to compensate for errors in the output of said pressure transducer; and d. display adapted to indicate the blood pressure of the patient.

21. Method for measuring blood pressure by medical personnel comprising:
- occluding the flow of blood in the limb of a patient until the point of obliteration of the pulse is detected using a pressure cuff arrangement;
- measuring electronically the pressure in the cuff arrangement as the pressure in the cuff arrangement is reduced to generate an output signal corresponding to the blood pressure of the patient;
- augmenting the output signal such that its response characteristic corresponds to the response characteristic of mercury in mercury-gravity pressure manometers;
- compensating for errors in measuring the pressure in the cuff; and
- displaying the blood pressure of the patient.

22. The method for measuring blood pressure according to claim 20, wherein the step of occluding the flow of blood includes increasing the pressure in an inflatable bladder of the pressure cuff arrangement to a point where no pulse is felt.

23. The method for measuring blood pressure according to claim 21, wherein the step of measuring the pressure in the cuff includes generating an electrical signal corresponding to the pressure in the cuff utilizing a pressure transducer.

24. The method for measuring blood pressure according to claim 22, wherein the step of augmenting the output includes low pass filtering the electrical signal from the pressure transducer.

25. The method for measuring blood pressure according to claim 23, wherein the step of compensating for errors includes generating an error correction signal to be combined with the electrical signal output from the pressure transducer.

26. The method for measuring blood pressure according to claim 24, wherein the error correction signal is generated by a microprocessor based upon the operating temperature of the pressure transducer.

27. The method for measuring blood pressure according to claim 20, further comprising storing the blood pressure values in a memory for historical trending and future reference.

28. The method for measuring blood pressure according to claim 20, wherein the step of displaying the blood pressure includes generating a graphical or numeric display of the blood pressure of the patient on a display.

29. Blood pressure measurement system for use by medical personnel comprising:
- pressure cuff system for a limb of a patient; and
- electronics package coupled to said pressure cuff system, the electronics package including a pressure transducer adapted to generate an output signal corresponding to the blood pressure of the patient, a filter adapted to augment the output signal of the pressure transducer such that its response characteristic corresponds to the response characteristic of mercury in mercury-gravity pressure manometers, a controller, a display coupled to said controller and adapted to indicate the blood pressure of the patient, and a capture button coupled to said controller, said capture button being operable to store the blood pressure of the patient in a memory of said controller and to display the blood pressure on said display when actuated.

30. An electronic blood pressure measurement system for use by medical personnel comprising:
- pressure cuff arrangement for manipulating blood flow in a limb of a patient;
- at least one pressure transducer coupled to the pressure cuff arrangement and adapted to generate an output signal corresponding to the blood pressure of the patient;
- filter for augmenting the output signal of said at least one pressure transducer such that its response characteristic corresponds to the response characteristic of mercury in mercury-gravity pressure manometers;
- display adapted to display the blood pressure of the patient;
- controller adapted to implement a plurality of functions including controlling the operation of said at least one pressure transducer and said filter, generating images on said display, and compensating for errors in the output of said at least one pressure transducer; and
- a capture button coupled to said controller, said capture button being operable to store the blood pressure of the patient in a memory of said controller and to display the blood pressure on said display when actuated.

* * * * *